United States Patent

Andes et al.

Patent Number: 5,985,020
Date of Patent: Nov. 16, 1999

[54] PLATE-LIKE TITANIUM DIOXIDE REDUCTION PIGMENT

[75] Inventors: Stefanie Andes, Maintal; Sabine Hock, Schaafheim; Günter Brenner, Griesheim; Dieter Brückner, Darmstadt; Andrea Heyland, Ober-Kainsbach; Matthias Kuntz, Seeheim; Karl Osterried, Dieburg; Gerhard Pfaff, Münster; Michael Schmelz, Kriftel, all of Germany

[73] Assignee: Merck Patent Gesellschaft Mit Beschrankter Haftung, Germany

[21] Appl. No.: 08/983,348

[22] PCT Filed: Apr. 25, 1997

[86] PCT No.: PCT/EP97/02133

§ 371 Date: Jan. 9, 1998

§ 102(e) Date: Jan. 9, 1998

[87] PCT Pub. No.: WO97/43347

PCT Pub. Date: Nov. 20, 1997

[30] Foreign Application Priority Data

May 9, 1996 [DE] Germany .................. 196 18 562

[51] Int. Cl.⁶ .................................................. C09C 1/36
[52] U.S. Cl. ................. 106/436; 106/415; 106/437; 106/438; 106/439; 106/441; 106/442; 106/446; 428/402
[58] Field of Search ............... 106/415, 437, 106/438, 439, 446, 441, 442, 404, 402

[56] References Cited

U.S. PATENT DOCUMENTS

| | | | |
|---|---|---|---|
| 3,395,203 | 7/1968 | Morita et al. | 264/141 |
| 3,767,443 | 10/1973 | Clark et al. | 106/415 |
| 3,861,946 | 1/1975 | Waitkins et al. | 428/404 |
| 4,978,394 | 12/1990 | Ostertag et al. | 106/404 |

FOREIGN PATENT DOCUMENTS 0 481 460 A2  4/1992  European Pat. Off. .
0 601 761 A1  6/1994  European Pat. Off. .

OTHER PUBLICATIONS

Derwent abstract 87–039671 of JP 61 295 234 A, Dec. 1986.
Derwent abstract 70–18273R of JP 45–6424 B, Nov. 1970.

*Primary Examiner*—Mark L. Bell
*Assistant Examiner*—Scott L. Hertzog
*Attorney, Agent, or Firm*—Millen, White, Zelano & Branigan, P.C.

[57] ABSTRACT

Plateletlike titanium dioxide reduction pigment consisting of titanium dioxide, titanium suboxides and, if desired, a further metal oxide or titanium oxynitride, obtainable by solidifying an aqueous solution of a thermally hydrolysable titanium compound on a continuous belt, detaching the resulting coat, coating the resulting titanium dioxide platelets, with or without drying in between, with further titanium dioxide by a wet method, drying and, if desired, calcining the material, and treating the material obtained with a reducing agent in a nonoxidizing gas atmosphere.

11 Claims, 1 Drawing Sheet

PLATE-LIKE TITANIUM DIOXIDE REDUCTION PIGMENT

BACKGROUND OF THE INVENTION

The invention relates to very thin, plateletlike titanium dioxide reduction pigments.

Plateletlike titanium dioxide reduction pigments are known. However, they are based on the use of mica as substrate. The titanium dioxide is precipitated onto the mica and is subsequently subjected to partial reduction to titanium suboxides. Reducing agents used are gaseous reducing agents, such as hydrogen and ammonia, or solid reducing agents, such as silicon or titanium. Some of these pigments also possess an additional top layer comprising silicon dioxide.

U.S. Pat. No. 4,948,631 describes a process for preparing particularly bluish pearl luster pigments by reducing titanium dioxide-coated mica pigments with ammonia at temperatures from 750 to 850° C.

JP H4-20 031 describes a process for producing a colored mica pigment by mixing a titanium dioxide-mica pigment with titanium and reducing the resulting mixture under reduced pressure at from 500 to 1000° C.

U.S. Pat. No. 4,623,396 describes a titanium dioxide-mica pigment consisting of mica, a first layer of titanium dioxide, titanium suboxides and titanium oxynitrides and a second layer of titanium dioxide.

Mica pigments are used widely in the printing and coating industries, in cosmetics and in polymer processing. They are distinguished by interference colors and a high luster. For the formation of extremely thin layers, however, mica pigments are not suitable, since the mica itself, as substrate for the metal oxide layers of the pigment, has a thickness of from 200 to 1200 nm. A further disadvantage is that the thickness of the mica platelets within a certain fraction defined by the platelet size in some cases varies markedly about a mean value. Moreover, mica is a naturally occurring mineral which is contaminated by foreign ions. Moreover, technically highly complex and time-consuming processing steps are required, including, in particular, grinding and classifying.

Pearl luster pigments based on thick mica platelets and coated with metal oxides have, owing to the thickness of the edge, a marked scatter fraction, especially in the case of relatively fine particle-size distributions below 20 $\mu$m.

As a substitute for mica it has been proposed to use thin glass flakes which are obtained by rolling of a glass melt with subsequent grinding. Indeed, interference pigments based on such materials exhibit color effects superior to those of conventional, mica-based pigments. Disadvantages, however, are that the glass flakes have a very large average thickness of about 10–15 $\mu$m and a very broad thickness distribution (typically between 4 and 20 $\mu$m), whereas the thickness of interference pigments is typically not more than 3 $\mu$m.

EP 0 384 596 describes a process in which hydrated alkali metal silicate is subjected at temperatures of 480–500° C. to the action of an air jet, forming bubbles with thin walls; the bubbles are subsequently comminuted to give plateletlike alkali metal silicate substrates with a thickness of less than 3 $\mu$m. However, the process is complex and the thickness distribution of the resulting platelets is relatively broad.

DE 11 36 042 describes a continuous belt method of preparing plateletlike or glitterlike oxides or oxide hydrates of metals of groups IV and V and of the iron group of the Periodic Table. In this method, a release layer comprising, for example, a silicone coating is first of all applied, if desired, to a continuous belt in order to facilitate the subsequent detachment of the metal oxide layer. Then a liquid film is applied which comprises a solution of a hydrolyzable compound of the metal which is to be converted into the desired oxide, and the film is dried and subsequently detached using a vibration device. The layer thickness of the platelets obtained is given as being 0.2 to 2 $\mu$m, although no concrete examples of this are cited.

EP 0 240 952 and EP 0 236 952 propose a continuous belt method of preparing different plateletlike materials, including silicon dioxide, aluminium oxide and titanium dioxide. In this method, a thin liquid film of defined thickness of a precursor of the plateletlike material is applied, via a roller system, to a smooth belt; the film is dried and detached from the belt, forming plateletlike particles. The particles are subsequently, if desired, calcined, ground and classified.

The thickness of the platelets obtained in accordance with the method described in EP 0 240 952 is relatively well defined, since the film is applied very uniformly, via a roller system, to the continuous belt, for example. The layer thickness of the platelets is given in the examples as being 0.3 to 3.0 $\mu$m. According to Example 1, a first roller is wetted with the precursor used by immersing this roller partially into a stock container which is filled with the precursor. The film is tranferred from this roller to a second, corotating roller which is in very close contact with the first roller. Finally, the film is rolled off from the second roller onto the continuous belt.

Disadvantages, however, are the use of very expensive precursor materials and, in particular, the increased requirements in terms of workplace safety which must be applied when organometallic compounds are used. The complete chemical conversion of the precursor into the desired layer material requires, in general, high heating of the film and of the belt material. In addition to the considerable thermal stress which this places on the belt material, the high energy consumption and the restriction on the process speed are highly disadvantageous for the economy of the method.

WO 93/08237 describes plateletlike pigments consisting of a plateletlike matrix comprising silicon dioxide, which may contain soluble or insoluble colorants and which is covered with one or more reflecting layers of metal oxides or metals. The plateletlike matrix is prepared by solidification of waterglass on a continuous belt.

DE 12 73 098 describes the preparation of a mother-of-pearl pigment by vapor deposition of ZnS, MgF$_2$, ZnO, CaF$_2$ and TiO$_2$ films onto a continuous belt. This process, however, like the process described in U.S. Pat. No. 4,879,140 in which plateletlike pigments with Si and SiO$_2$ layers are obtained by plasma deposition from SiH$_4$ and SiCl$_4$, is associated with very high expenditure on apparatus.

Despite numerous attempts, it has not hitherto been possible to develop any economic process for preparing very thin plateletlike titanium dioxide pigments having a layer thickness of less than 500 nm.

SUMMARY OF THE INVENTION

An object of the invention is to provide a highly lustrous plateletlike titanium dioxide reduction pigment having a layer thickness of less than 500 nm and a layer-thickness tolerance of less than 10%.

This object is achieved by a plateletlike titanium dioxide reduction pigment consisting of titanium dioxide, titanium suboxides and, if desired, a further metal oxide or titanium oxynitride, obtainable by preparing a plateletlike titanium dioxide by solidifying a liquid precursor on a continuous belt, detaching the resulting layer, coating the resulting titanium dioxide platelets, without drying in between, with further titanium dioxide by a wet method, drying and, if desired, calcining the material, and treating the material obtained with a reducing agent in a nonoxidizing gas atmosphere.

This object is additionally achieved in accordance with the invention by a process for preparing the novel pigments, consisting of titanium dioxide, titanium suboxides and, if desired, a further metal oxide or titanium oxynitride, in which a precursor of the plateletlike titanium dioxide is applied as a thin film to a continuous belt the liquid film is solidified by drying, during the course of which the titanium dioxide is developed from the precursor by means of a chemical reaction, the resulting layer is subsequently detached from the belt and washed, the titanium dioxide platelets obtained, with or without drying in between, are suspended in water and coated with further titanium dioxide, the coated titanium dioxide platelets are separated out from the aqueous suspension, dried and, if desired, calcined, and are treated with a reducing agent in a nonoxidizing gas atmosphere at elevated temperatures.

In a particular embodiment of the process, the titanium dioxide platelets detached from the belt are dried, are coated further with titanium dioxide using alternative methods, for example CVD methods, and are treated with a reducing agent in a nonoxidizing gas atmosphere at elevated temperatures. The term CVD methods refers here to coating in the gas phase in a fluidized-bed reactor, as is described in EP 0 045 851 and EP 0 106 235 for the preparation of pearl luster pigments.

This object is additionally achieved in accordance with the invention by a process for preparing the novel pigments, consisting of titanium dioxide, titanium suboxides and, if desired, a further metal oxide or titanium oxynitride, in which a precursor of the plateletlike titanium dioxide is applied as a thin film to a continuous belt the liquid film is solidified by drying, during the course of which the titanium dioxide is developed from the precursor by means of a chemical reaction, the resulting layer is subsequently detached from the belt and washed, the titanium dioxide platelets are separated out from the aqueous suspension, dried and, if desired, calcined, and are treated with a reducing agent in a nonoxidizing gas atmosphere at elevated temperatures.

The invention additionally relates to the use of the novel pigments for pigmenting paints, printing inks, plastics, cosmetics and glazes for ceramics and glass.

For this purpose they can be employed as mixtures with commercially available pigments, for example inorganic and organic absorption pigments, metal-effect pigments and LCP pigments.

The novel pigments are based on plateletlike titanium dioxide particles. These platelets have a thickness of between 10 nm and 500 nm, preferably between 40 and 150 nm. The extent in the two other dimensions is between 2 and 200 μm and, in particular, between 5 and 50 μm.

The titanium dioxide layer, which is applied to the plateletlike titanium dioxide particles by a wet method, possesses a thickness of from 5 to 300 nm, preferably between 5 and 150 nm.

The precursor used for preparing the titanium dioxide platelets on the continuous belt comprises aqueous solutions of thermally hydrolysable titanium compounds. A preferred precursor is aqueous titanium tetrachloride solution. The concentration of the titanium salt in these solutions is from 7 to 30% by weight, preferably from 8 to 15% by weight.

The additional metal oxide which can be present alongside titanium dioxide and titanium suboxides in the novel pigment is the oxidation product of the reducing agent employed. This metal oxide is present in the novel pigment in a concentration of from 1 to 20% by weight, preferably from 1 to 5% by weight.

The reducing agents employed are gaseous reducing agents such as, for example, hydrogen, or solid reducing agents in the form of metal powders, alloys of metals, metal borides, metal carbides or metal suicides. Preference is given to the powders of the metals boron, aluminium, silicon, zinc and iron, and especially to silicon.

The titanium dioxide pigment and the reducing agent are mixed in a ratio of from 100:1 to 5:1. In a particular embodiment, the novel pigment can also contain carbon black, which is either applied directly to the plateletlike titanium dioxide particles or is precipitated onto the plateletlike titanium dioxide particles together with the titanium dioxide in a wet method. Details are described in DE 195 02 231, DE 42 22 372 and U.S. Pat. No. 4,076,551.

Figure 1:
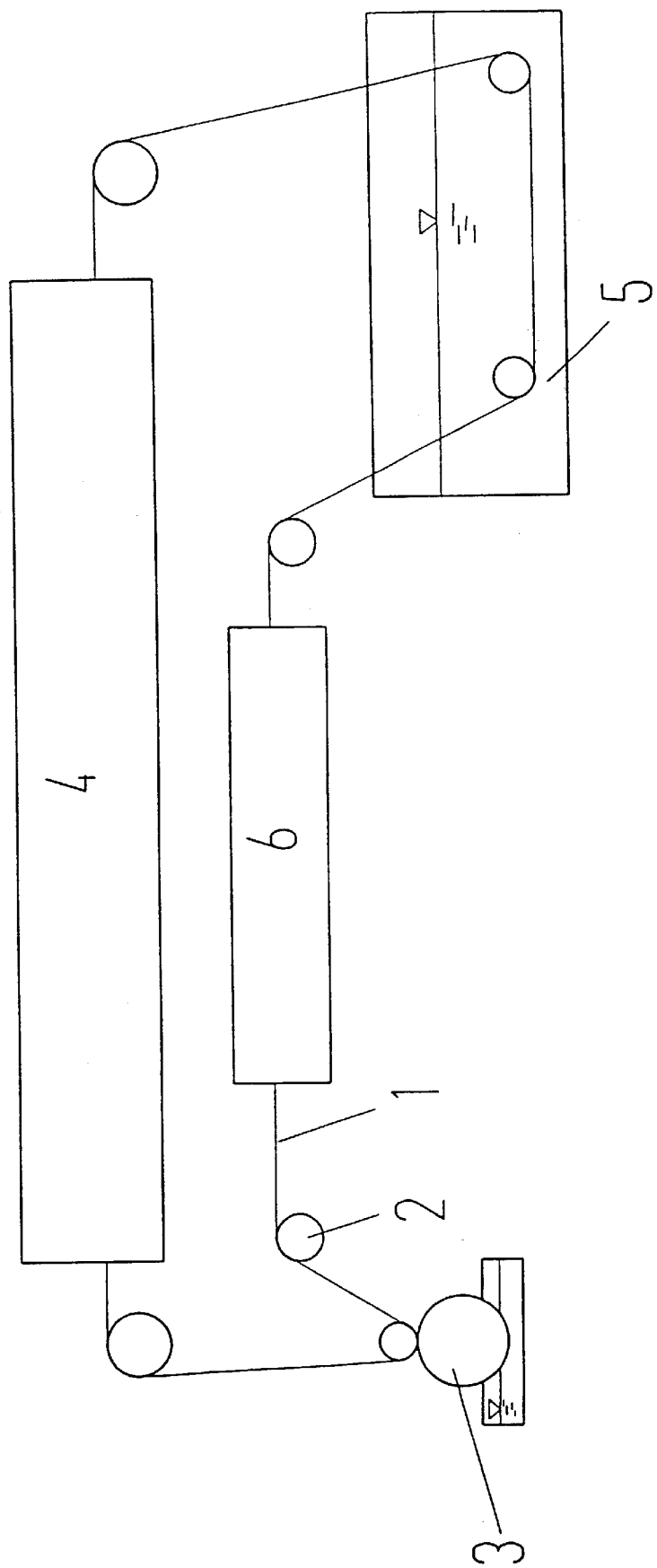
FIG. 1 shows the belt method of producing the instant particles.

The novel pigments are prepared in a three-stage process. In the first stage, plateletlike titanium dioxide particles are prepared with the aid of a continuous belt.

First of all, the belt method will be explained with reference to FIG. 1.

The continuous belt 1, which is guided via a roller system 2, passes through an applicator unit 3 in which it is coated with a thin film of the precursor. Suitable applicator units which can be employed are roller applicators and also flow-type units. The belt speed is between 2 and 400 m/min, preferably 5–200 m/min.

In order to achieve uniform wetting of the plastics belt it is expedient to add a commercially available wetting agent to the coating solution or to activate the surface of the belt by flame treatment, corona treatment or ionization.

The coated belt passes subsequently through a drying section 4 in which the layer is dried at temperatures betweeen 30 and 200° C. As dryers it is possible, for example, to employ commercially available infrared, circulating-air jet and UV dryers.

After passing through the drying section, the belt is passed through the detachment baths 5 containing an appropriate detachment medium, for example deionized water, where the dried layer is removed from the belt. The detachment procedure is supported by additional devices, for example jets, brushes or ultrasound.

In a subsequent dryer 6, the belt is dried before being coated again.

The continuous belt should be made from a chemically and thermally resistant plastic in order to ensure an adequate service life and high drying temperatures. Suitable materials for the belt include polyethylene terephthalate (PET) or other polyesters and polyacrylates.

The film width is typically between a number of centimeters and two or more meters. The thickness is between 10 µm and a number of millimeters, these two parameters being optimized in respect of the particular requirements.

Further details of continuous belt methods are known from U.S. Pat. No. 3,138,475, EP 0 240 952 and WO 93/08237.

In a second process stage, the titanium dioxide platelets detached from the belt are coated, without being dried beforehand, with further titanium dioxide in accordance with known methods. It is preferred to use the method described in U.S. Pat. No. 3,553,001.

An aqueous titanium salt solution is added slowly to a suspension of the titanium dioxide platelets, which is heated at about 50–100° C., in particular 70–80° C., and a substantially constant pH of about 0.5–5, in particular about 1.5–2.5, is maintained by simultaneous metered addition of a base, for example aqueous ammonia solution or an aqueous alkali metal hydroxide. As soon as the desired layer thickness of the $TiO_2$ precipitation has been reached, the addition of the titanium salt solution is stopped.

This method, which is also called the titration method, is notable for the fact that it avoids an excess of titanium salt. This is achieved by supplying to the hydrolysis, per unit time, only that quantity (of titanium salt) as is required for uniform coating with the hydrated $TiO_2$ and as can be adsorbed per unit time by the available surface of the particles to be coated. There is, therefore, no formation of hydrated titanium dioxide particles which are not deposited on the surface to be coated. The quantity of titanium salt added per minute is, in this case, in the order of from about 0.01 to $20 \cdot 10^{-5}$ mol of titanium salt per square meter of surface to be covered.

In a third process stage, the plateletlike titanium dioxide particles, which have been coated with further titanium dioxide by a wet method, are subjected to a reduction process as is known for the preparation of titanium dioxide reduction pigments. Preference is given to using the process described in WO 93/19131.

The titanium dioxide particles are mixed intensively with the above-described solid reducing agents in a ratio of from 100:1 to 5:1 and are treated in a nonoxidizing atmosphere at temperatures of more than 600° C., preferably in the range from 700 to 1100° C., for more than 10 minutes, preferably for 15 to 60 minutes. Nonoxidizing gases used are nitrogen, argon, helium or carbon dioxide, preference being given to nitrogen or argon.

The reduction reaction is accelerated in the presence of a halide. Preference is given to alkali metal and alkaline earth metal chlorides, for example lithium chloride, sodium chloride, potassium chloride, magnesium chloride and calcium chloride, or other metal chlorides, for example iron(II) and iron(III) chloride, nickel chloride, copper chloride, manganese chloride and chromium chloride. Calcium chloride is employed with particular preference. Based on the titanium dioxide pigment used, from 0.1 to 40% by weight, preferably from 0.5 to 10% by weight, of chloride is employed.

As gaseous reducing agents it is possible to use hydrogen—nitrogen mixtures or ammonia. It is preferred to use a hydrogen-nitrogen mixture with a hydrogen content of 3% by volume.

The novel pigment can in addition be coated with firmly adhering inorganic or organic colorants of low solubility. It is preferred to use color lakes and, in particular, aluminium color lakes. To this end an aluminium hydroxide coat is applied by precipitation and in a second step is laked with a color lake. The process is described in more detail in DE 24 29 762 and DE 29 28 287.

Also preferred is an additional coating with complex salt pigments, especially cyanoferrate complexes, for example Prussian blue and Turnbull's blue, as is described in EP 0 141 173 and DE 23 13 332.

The novel pigment can also be coated with organic dyes and, in particular, with phthalocyanine or metal phthalocyanine and/or indanthrene dyes according to DE 40 09 567. For this purpose a suspension of the pigment in a solution of the dye is prepared, and this suspension is then brought together with a solvent in which the dye is of low or zero solubility.

For an additional coating it is also possible, furthermore, to employ metal chalcogenides or metal chalcogenide hydrates and carbon black.

It is additionally possible to subject the pigments to an aftercoating or aftertreatment which further increases the light stability, weathering resistance and chemical stability or facilitates the handling of the pigment, especially its incorporation into different media. Examples of suitable aftercoating and/or aftertreatment techniques are those described, for example, in DE-C 22 15 191, DE-A 31 51 354, DE-A 32 35 017 or DE-A 33 34 598. Owing to the fact that the properties of the novel pigments are already very good without these additional measures, these optional additionally applied substances make up only from about 0 to 5% by weight, in particular from about 0 to 3% by weight, of the overall pigment.

Relative to the titanium dioxide reduction pigments known to date, the novel pigment is distinguished by a higher luster and a highly uniform thickness. The standard deviation designated as the thickness tolerance is not more than 10%. Owing to the plane-parallel surface and the narrow thickness tolerance of the pigment particles, very high cleanness of color and a very high tinctorial strength are achieved.

In terms of the thickness, the novel pigment represents the ideal state which is the most which can be achieved with pearl luster pigments, since it consists solely of optically functional layers and is devoid of the otherwise customary support material, for example mica or glass flakes, which makes no contribution to the optical effect. Owing to the thickness of the mica, mica pigments possess a thickness which, for a given thickness of the functional layers, is greater by a factor of 25. In terms of the technical applications this results in intrinsic advantages which can be achieved by no other conventional pearl luster pigment. For example, layers can be made thinner and the quantity of pigment required can be reduced since, owing to the absence of the support material "filler", the pigments are more optically active.

EXAMPLES

The examples given below are intended to illustrate the invention without limiting it.

EXAMPLE 1

A circulating belt of polyethylene terephthalate (width: 0.3 m, speed: 20 m/min) is coated with a 20% titanium tetrachloride solution by means of a counter rotating applicator roll. The coating solution contains 0.3% by weight of surfactant (DISPERSE-AYD W-28, Manufacturer: DANIEL PRODUCTS COMPANY). The aqueous film on the belt is dried in a drying section by subjecting it to hot air at 70° C. and the layer formed is detached from the belt in a detachment basin filled with deionized water. The plateletlike titanium dioxide particles are filtered and washed with deionized water. The platelets have a silvery luster and a layer thickness of 100±10 nm. For coating with further titanium dioxide, they are redispersed in deionized water.

2l of the dispersion (solids content: 15 g of $TiO_2$) are heated to 75° C. and adjusted with dilute hydrochloric acid to a pH of 1.8.

4.3 g of $SnCl_4.5H_2O$ are dissolved in 29 ml of HCl, and the solution is made up to 290 ml with distilled water and stirred for 10 minutes.

The $SnCl_4$ solution is added to the $TiO_2$ suspension at a rate of 3 ml/min, during which the pH is kept constant at 1.8 with 32% NaOH solution. Following the covering with $SnO_2$, the suspension is stirred at a constant temperature and constant pH for 15 minutes.

A 40% aqueous titanium tetrachloride solution is then metered at a rate of 3 ml/min and the pH is still kept constant at 1.8 with 32% of NaOH.

The addition of $TiCl_4$ is continued until the desired first- or higher-order interference color is achieved. The pigment obtained is filtered off, washed with deionized water until salt-free, dried and calcined at 750° C. The color properties do not alter greatly as a function of the calcination temperature, and in each case pearl lustre pigments of rutile structure are obtained.

10 g of titanium dioxide pigment with a red interference color are intensively mixed with 0.2 g of powdered silicon (particle size: <150 μm, manufacturer: Merck KGaA) and the mixture is calcined in a tube furnace under nitrogen at 850° C. for a period of 45 minutes.

A pigment is obtained with a black-red powder color and a brilliant red interference color.

EXAMPLE 2

2l of the dispersion of $TiO_2$ platelets (solids content: 15 g of $TiO_2$) from Example 1 are heated to 75° C. and adjusted with dilute hydrochloric acid to a pH of 2.2.

A 40% aqueous titanium tetrachloride solution is then metered at a rate of 3 ml/min and the pH is still kept constant at 2.2 with 32% of NaOH.

The addition of $TiCl_4$ is continued until the desired first- or higher-order interference color is achieved. The pigment obtained is filtered off, washed with deionized water until salt-free, dried and calcined at 750° C. The color properties alter to a much greater extent as a function of the calcination temperature than in Example 1 owing to the anatase-rutile conversion, which begins at about 600° C. and is finished at 750° C. It is therefore possible to prepare $TiO_2$ pearl luster pigments, free from Sn, in the rutile modification.

10 g of titanium dioxide pigment with a red interference color are intensively mixed with 0.2 g of powdered silicon (particle size: <150 μm, manufacturer: Merck KGaA) and the mixture is calcined in a tube furnace under nitrogen at 850° C. for a period of 45 minutes.

A pigment is obtained with a dark-red powder color and a black-red interference colour.

EXAMPLE 3

2l of the dispersion of $TiO_2$ platelets (solids content: 15 g of $TiO_2$) from Example 1 are heated to 75° C. and adjusted with dilute hydrochloric acid to a pH of 2.2.

A 40% aqueous titanium tetrachloride solution is then metered at a rate of 3 ml/min and the pH is still kept constant at 2.2 with 32% of NaOH.

The addition of $TiCl_4$ is continued until the desired first- or higher -order interference color is achieved. The pigment obtained is filtered off, washed with deionized water until salt-free, dried and calcined at 750° C. The colour properties alter to a much greater extent as a function of the calcination temperature than in Example 1 owing to the anatase-rutile conversion, which begins at about 600° C. and is finished at 750° C. It is therefore possible to prepare $TiO_2$ pearl lustre pigments, free from Sn, in the rutile modification.

10 g of titanium dioxide pigment with a red interference color are calcined in a tube furnace under nitrogen at 850° C. for a period of 45 minutes in a nitrogen-hydrogen atmosphere with a hydrogen content of 3% by volume.

A pigment is obtained with a dark-red powder color and a black-red interference color.

We claim:

1. A platelet-shaped titanium dioxide reduction pigment comprising titanium dioxide, a titanium suboxide and optionally a further metal oxide or titanium oxynitride, obtained by solidifying an aqueous solution of a thermally hydrolyzable titanium compound on a continuous belt, detaching the resulting layer, coating the resulting titanium dioxide platelets, without drying in between, with further titanium dioxide by a wet method, drying optionally calcining the material, and optionally treating the material obtained with a reducing agent in a nonoxidizing gas atmosphere.

2. A titanium dioxide reduction pigment according to claim 1, the further metal oxide is $Li_2O$, $Na_2O$, $K_2O$, MgO, CaO, $B_2O_3$, $Al_2O_3$, $SiO_2$, ZnO, $SnO_2$ or $Fe_2O_3$.

3. A titanium dioxide reduction pigment according to claim 1, wherein the aqueous solution of a thermally hydrolysable titanium compound is an aqueous titanium tetrachloride solution.

4. A process for the preparation of a titanium dioxide reduction pigment according to claim 1, comprising
    applying an aqueous solution of a thermally hydrolyzable titanium compound as a thin film to a continuous belt,
    solidifying the liquid film by drying, during the course of which the titanium dioxide is developed from the solution by means of a chemical reaction,
    detaching the resulting layer from the belt and washing,
    suspending in water the titanium dioxide platelets obtained, without drying in between, and coating with further titanium dioxide,
    separating the titanium dioxide platelets from the aqueous suspension, optionally drying and calcining, and
    treating with a reducing agent in a nonoxidizing gas atmosphere at elevated temperatures.

5. A process according to claim 4, wherein the aqueous solution of a thermally hydrolysable titanium compound is an aqueous titanium tetrachloride solution.

6. A process according to claim 4, wherein the reducing agent is an alkali metal, B, Al, Si, Zn, Fe, LiH, $CaH_2$, $Al_4C_3$, $Mg_2Si$, $MgSi_2$ or $CaSi_2$.

7. A process according to claim 4 wherein the reducing agent is ammonia or a hydrogen-nitrogen mixture.

8. Process according to claim 4, characterized in that the further titanium dioxide is applied to the titanium dioxide platelets in a fluidized-bed reactor by CVD.

9. In a paint, printing ink, plastic, cosmetic or glaze for ceramics and glass containing a pigment, the improvement wherein the pigment is one according to claim 1, optionally employed as mixtures with a commercially available pigment.

10. A platelet-shaped titanium dioxide reduction pigment comprising titanium dioxide, at least one titanium suboxide and optionally a further metal oxide or titanium oxynitride, having a planeparallel surface, a thickness tolerance of lower than 10% and a layer thickness of lower than 500 nm.

11. In a paint, printing ink, plastic, cosmetic, ceramic or glass pigmented with a pigment, the improvement wherein the pigment is one according to claim 10.

* * * * *